United States Patent
Prasad et al.

(10) Patent No.: US 7,444,291 B1
(45) Date of Patent: Oct. 28, 2008

(54) SYSTEM AND METHOD FOR MODELING OF HEALTHCARE UTILIZATION

(75) Inventors: Badri N. Prasad, St. Paul, MN (US); Louise H. Anderson, Bloomington, MN (US); Felix Friedman, Eden Prairie, MN (US); Gerald L. Lutgen, St. Paul, MN (US)

(73) Assignee: Ingenix, Inc., Eden Prairie, MN (US)

( * ) Notice: Subject to any disclaimer, the term of this patent is extended or adjusted under 35 U.S.C. 154(b) by 529 days.

(21) Appl. No.: 09/635,911

(22) Filed: Aug. 10, 2000

(51) Int. Cl.
*G06Q 10/00* (2006.01)
(52) U.S. Cl. .................. 705/2; 705/3; 705/4; 600/300; 600/301
(58) Field of Classification Search ................. 705/2–4; 600/300–301; 706/924
See application file for complete search history.

(56) References Cited

U.S. PATENT DOCUMENTS

| | | | | |
|---|---|---|---|---|
| 5,018,067 A | * | 5/1991 | Mohlenbrock et al. | 600/300 |
| 5,486,999 A | * | 1/1996 | Mebane | 705/2 |
| 5,557,514 A | * | 9/1996 | Seare et al. | 705/2 |
| 5,706,441 A | * | 1/1998 | Lockwood | 705/3 |
| 5,819,228 A | * | 10/1998 | Spiro | 705/2 |
| 5,835,897 A | | 11/1998 | Dang | 705/2 |
| 5,845,254 A | * | 12/1998 | Lockwood et al. | 705/2 |
| 5,970,463 A | | 10/1999 | Cave et al. | 705/3 |
| 5,976,082 A | * | 11/1999 | Wong et al. | 600/300 |
| 6,061,657 A | * | 5/2000 | Whiting-O'Keefe | 705/2 |
| 6,223,164 B1 | * | 4/2001 | Seare et al. | 705/2 |
| 6,266,645 B1 | * | 7/2001 | Simpson | 705/3 |
| 6,370,511 B1 | | 4/2002 | Dang | 705/3 |
| 6,385,589 B1 | | 5/2002 | Trusheim et al. | |
| 6,581,204 B2 | | 6/2003 | DeBusk et al. | |
| 6,629,095 B1 | | 9/2003 | Wagstaff et al. | |
| 6,802,810 B2 | | 10/2004 | Clarniello et al. | |
| 2001/0020229 A1 | * | 9/2001 | Lash | 705/3 |
| 2002/0004725 A1 | * | 1/2002 | Martin et al. | 705/2 |
| 2003/0167189 A1 | | 9/2003 | Lutgen et al. | |
| 2003/0195772 A1 | * | 10/2003 | Meek et al. | 705/2 |

(Continued)

FOREIGN PATENT DOCUMENTS

CA 2216681 3/1998

(Continued)

OTHER PUBLICATIONS

The Burden of Illness in Canada, accessed at www.burdenofilness.ca, Dec. 3, 2003.*

(Continued)

*Primary Examiner*—C Luke Gilligan
*Assistant Examiner*—Vivek Koppikar
(74) *Attorney, Agent, or Firm*—Dorsey & Whitney LLP

(57) ABSTRACT

A system and method for modeling healthcare utilization based on usage data from physician claims, hospital claims, and pharmacy claims. The method includes extracting from a claims file the portion of the data from a base period that is relevant to modeling healthcare utilization in a target period by computing a utilization score based on the usage data. The models may be used concurrently by calibrating them with the base period equal to the target period and they may be also be used prospectively by calibrating the models with the target period representing a future time period.

28 Claims, 10 Drawing Sheets

U.S. PATENT DOCUMENTS

2004/0199332 A1* 10/2004 Iliff .............................. 702/19

FOREIGN PATENT DOCUMENTS

| JP | 2005-275886 | * | 10/2005 |
| JP | 2006-48554 | * | 2/2006 |

OTHER PUBLICATIONS

"Automated Systems Help Risk Managers Forecast Loses"; by Beth Wade; Corporate Cashflow, vol. 13, No. 8, p. 10-12, Jul. 1992, ISSN: 1040-0311, Dialog ID No. 00362536, From Dialog File 485 (Accounting and Tax Database).*

Alexandre, Leslie M., "High-Cost Patients in a Fee-For-Service Medical Plan, The Case for Earlier Intervention," *Medical Care*, Feb. 1990, vol. 28, No. 2, pp. 112-123.

Clark, Daniel O., et al., "A chronic Disease Scare with Empirically Derived Weights," *Medical Care*, vol. 33, No. 8, pp. 783-795.

Roblin, Douglas W., et al., "A Low-Cost Approach to Prospective Identication of Impending High-Cost Outcomes," *Medical Care*, vol. 37, No. 11, pp. 1155-1163.

Steen, Paul M., "Approaches to Predictive Modeling," *Ann Thorac Surg* 1994:58:1836-40.

Joseph P. Newhouse, et al., "Risk Adjustment and Medicare: Taking a Closer Look", Health Affairs—vol. 16, No. 5, 1997, pp. 26-43.

* cited by examiner

SYSTEM AND METHOD FOR MODELING OF HEALTHCARE UTILIZATION

TECHNICAL FIELD

The present invention relates to a system and method for modeling utilization of healthcare resources by a given member of a healthcare or insurance plan. More particularly, it relates to a system and method for modeling concurrent or prospective healthcare utilization in a target period based on physician claims, hospital claims, and pharmacy claims from a prior base period of experience.

BACKGROUND

Healthcare costs currently represent approximately 13 percent of the United States Gross National Product, and they continue to rise at a rapid pace. Managed healthcare systems are faced with the challenges of controlling the soaring costs of healthcare delivery and properly allocating healthcare resources. Both of these tasks are facilitated by a tool that explains prior healthcare utilization and provides an accurate estimate of future healthcare costs and utilization by the various members of the plan.

When a member of a healthcare plan receives care from healthcare providers, information regarding the care received is provided to plan administrators in documents commonly referred to as claims. Predominantly, this information is provided in the following three types of claims: physician claims, hospital claims, and pharmacy claims. These claims are the documents that are submitted to the healthcare plan by physicians, hospitals, or pharmacies to receive reimbursement for care provided to the plan member. These documents generally contain coded data that provides information regarding the care received by the plan member. These claims are processed by the healthcare plan and, where appropriate, payment is transmitted to the healthcare provider. For purposes of this specification, the phrase "physician claim" is used to refer to any professional service claim (e.g., optometrist) submitted to a health plan, typically on a HCFA 1500 form or its equivalent, and the phrase "hospital claim" is used to refer to any facility claim (e.g., outpatient surgery center) submitted to a health plan, typically on a UB92 form or its equivalent.

The healthcare utilization modeling methods of the prior art sacrifice reliability because they use only a portion of the readily available information, use portions of the information that do not reliably model utilization, or combine information in an unreliable way. There is a need in the art for a system and method for more reliably modeling healthcare utilization based on the data readily available in claims submitted to a health plan by healthcare providers.

The following materials serve as background for the present application and provide further information on some of the classification systems discussed in this specification: *Physician's Current Procedure Terminology CPT '94*, published by the American Medical Association, *Code it Right Techniques for Accurate Medical Coding*, published by Medicode, Inc., *HCPCS 1994 Medicare's National Level II Codes*, published by Medicode, Inc., *Med-Index ICD 9 CM Fourth Edition* 1993, published by Med-Index, each of which is hereby incorporated by reference.

BRIEF SUMMARY OF THE INVENTION

The present invention provides a system and method for modeling healthcare utilization during a target period based on usage data from physician claims, hospital claims, and pharmacy claims, during a base period. The method includes calculating a number representing the burden of illness for the member based on the provider claims, and computing a score for the member based on the burden of illness and at least one explanatory variable. The models may be used concurrently by calibrating them with the base period equal to the target period and they may be also be used prospectively by calibrating the models with the target period representing a future time period. The invention is highly flexible due the fact that the basic model structure is modular. By adding, removing, or exchanging elements of the model, one can use a wide variety of data sources in the model and can accommodate the needs of a diverse set of healthcare utilization applications.

DETAILED DESCRIPTION

Figure 1:
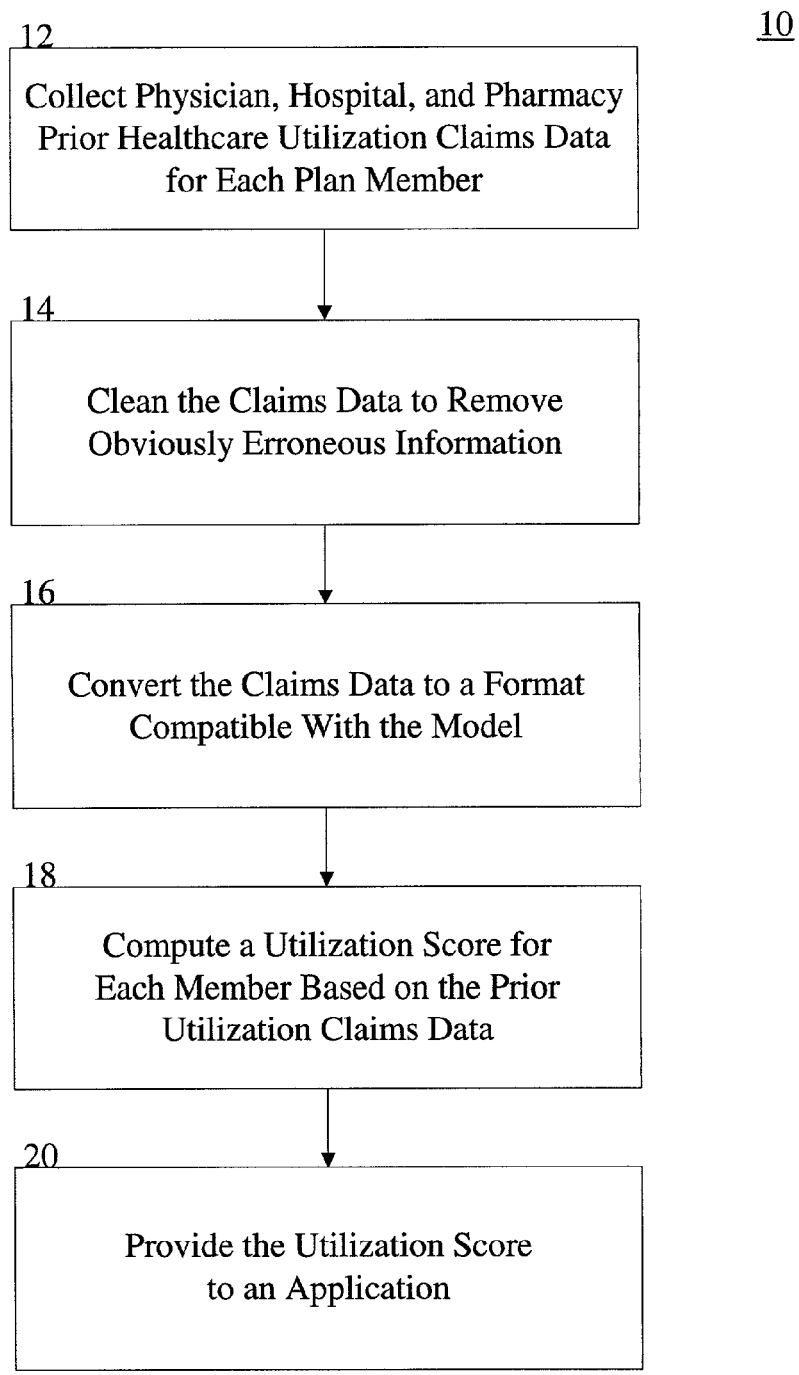
FIG. 1 is a block diagram illustrating an embodiment of the healthcare resources modeling method of the present invention.

FIG. 1 shows a block diagram illustrating one embodiment of the healthcare resources modeling method 10 of the present invention. As shown in FIG. 1, generally the healthcare resources modeling method 10 includes collecting physician, hospital, and pharmacy claims data for each plan member (block 12), cleaning the claims data to remove obviously erroneous information (block 14), converting the claims data to a format compatible with the model (block 16), computing a utilization score for each member (block 18), and providing the computed utilization scores to a secondary application for further processing (block 20). Each of these aspects of the present invention will be described in further detail below. In various embodiments of the present invention, as described below, one or more of these blocks may be omitted.

The healthcare resources modeling method 10 of the present invention has two major modes of operation. First, the method can be used in a prospective manner to predict future healthcare utilization. In this mode of operation, past claims data containing known healthcare utilization patterns is used to predict utilization for a future time period. For purposes of this application, the period of time over which the past claims data is collected will be referred to as the "base period," and the future period of time for which a prediction of healthcare utilization is derived will be referred to as the "target period." Second, the method can be used in a concurrent manner to prepare a summary of the base period claims data. In other words, the model is applied to the claims for the base period to generate summary information regarding utilization of healthcare resources by members during that time period. In the concurrent mode of operation, the healthcare resources modeling method 10 is not used to predict future utilization, but it is used to provide information on the base period. In other words, the base period and the target period are one and the same. The phrase "healthcare resources" is used in this application to refer to total healthcare cost, or its components, or a probability of an event, such as a complication, an emergency room visit, or a hospital admission.

As shown in block 12, the healthcare resources modeling method 10 involves collecting or extracting claims data from a central database, including a compilation of claims data over a desired time period (i.e., the base period). The claims from the base period are the source of prior healthcare utilization data. The base period may be fixed within the healthcare resources modeling method 10, or it may be a variable that is entered by an operator. In one embodiment of the present invention, the base period is twelve months. In other embodiments, the base period is more or less than twelve months, depending on the needs of the subsequent application. For example, for use with an underwriting application, described in more detail below, a minimum of six months of claims data is required. In another embodiment, all claims data is collected regardless of the claim date. In other words, depending on the application, claims data over any desirable time period may be used with the healthcare resources modeling method 10 of the present invention.

The claims data available for use in performing the healthcare resources modeling method 10 includes physician claims, hospital claims, and pharmacy claims for each plan member. The term "medical claims," as used in this application, refers to a combination of both physician claims and hospital claims. The claims contain the information submitted to a health plan by a provider requesting payment of fees or costs of services provided to a plan member. The claims contain information about the plan member and information describing the types of services provided and the dates such services were provided. Each type of claim includes several fields of information. In one embodiment of the present invention, the important fields in a physician claim include the date of service, the physician provider identification, the reason for the visit, and a description of the service or services provided. The reason for the visit is typically represented by an International Classification of Diseases ("ICD") code. The description of the service provided in a physician claim or a hospital claim typically takes one of two formats, a Common Procedural Terminology ("CPT") code (promulgated by the American Medical Association), or a Health Care Procedural Code ("HCPC") (promulgated by the Health Care Financing Administration). In other embodiments, other fields from a physician claim are also used. Typical fields included in a physician claim, many of which may be used in performing the healthcare resources modeling method 10, are generally known to those of skill in the art.

In one embodiment of the present invention, the important fields in a hospital claim include the date of service, the hospital provider identification, the reason for the visit, and a description of the service provides. The reason for the visit and the description of the service provided, in a hospital claim, typically is coded using the same systems discussed above with respect to physician claims. In other embodiments, other fields from a hospital claim are also used. Typical fields included in a hospital claim, many of which may be used in performing the healthcare resources modeling method 10, are generally known to those of skill in the art.

In one embodiment of the present invention, the important fields in a pharmacy claim include the date of fill, the pharmacy provider identification, the prescribing physician provider identification, and a description of the medication, generally in the form of a National Drug Code ("NDC"). In other embodiments, other fields from a pharmacy claim are also used. Typical fields included in a pharmacy claim, many of which may be used in performing the healthcare resources modeling method 10, are generally known to those of skill in the art.

In one embodiment, the collection process (block 12) is performed on a computer by executing software to locate and transfer data from a central database (or multiple databases) or from a mass storage device. In another embodiment of the present invention, the collection process is performed manually by a person collecting hardcopies of the necessary claims and entering the data into a database. In a first embodiment of the present invention, data from both medical claims and pharmacy claims is collected for use by the healthcare resources modeling method 10. In a second embodiment, only data from the pharmacy claims is collected for use by the healthcare resources modeling method 10 of the present invention. In a third embodiment, only data from the medical claims is collected for use by the present invention.

After collecting the claims data for the base period, the data is cleaned to remove obviously erroneous information (represented by block 14 in FIG. 1). The cleaning process involves checking each claim for information that is clearly incorrect. For example, in one embodiment, all maternity claims are checked to verify that the member's gender identified in the claim is female, and that the member's age is within an acceptable range. The cleaning process involves checking one field of the claims against predetermined allowable ranges for other fields or information within that claim. In one embodiment of the present invention, the claims shown in Table I below are examined for the specified types of erroneous information.

TABLE 1

| Claims Subjected to Cleaning Process | |
|---|---|
| Claim Type | Description |
| Maternity | Check age and gender for acceptable values |
| Prostate Cancer | Check age and gender for acceptable values |
| Multiple Sclerosis | Check age to verify that it is greater than 10 years |
| Cystic Fibrosis | Check age to verify that it is less than 40 years |

Persons of skill in the art can readily imagine other cleaning checks to perform on the data to identify erroneous information. In one embodiment, the cleaning process (block 14) is performed on a computer by executing software to detect and correct erroneous information. In another embodiment, the cleaning process (block 14) is performed manually by a person reviewing specified types of claims for erroneous information. In another embodiment of the present invention, the cleaning process (block 14) is not performed and any erroneous information present in the claims is not cleaned or corrected.

Figure 2:
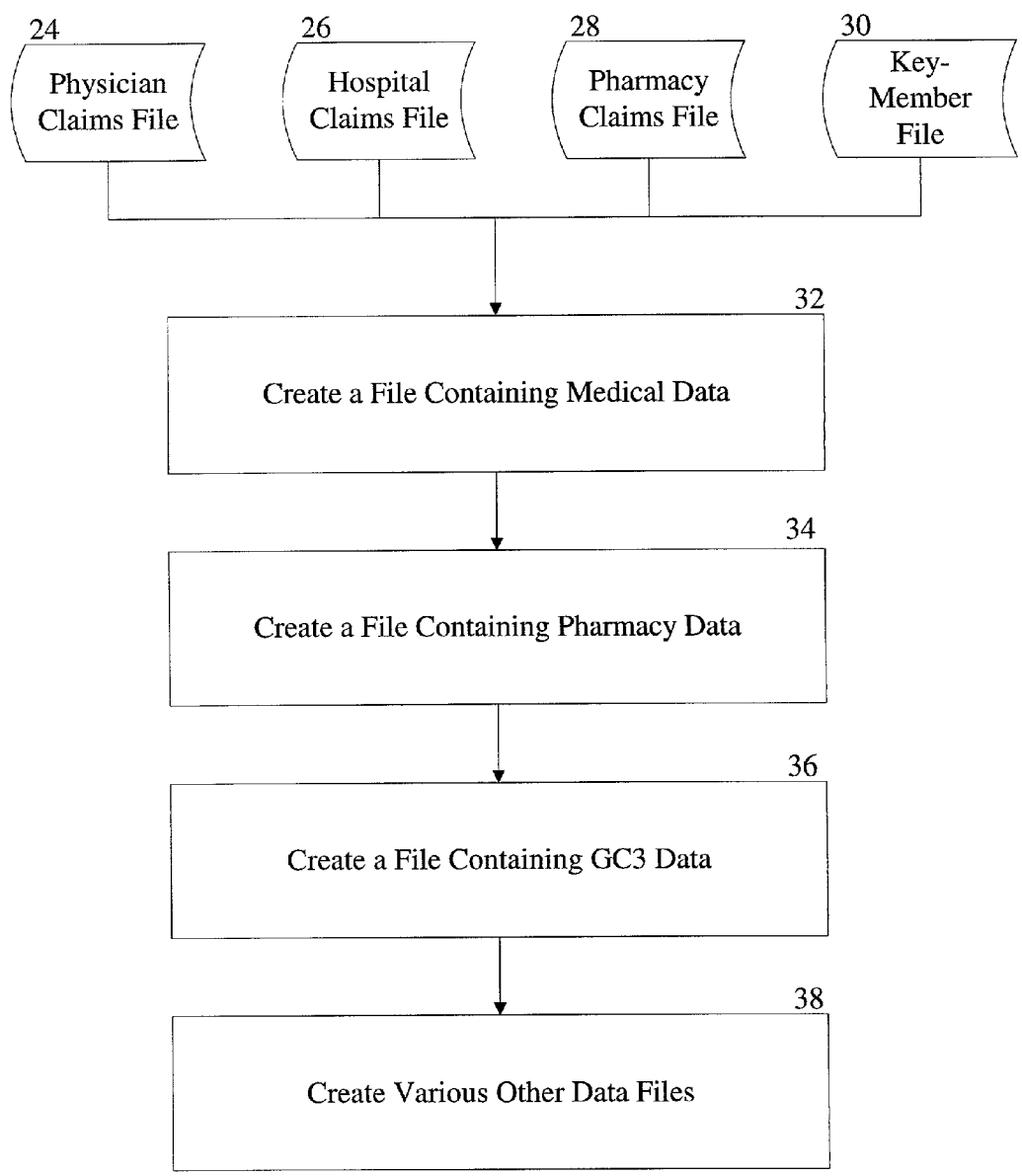
FIG. 2 is a block diagram showing various data files created from provider claims data for use in one embodiment of the healthcare resources modeling method of the present invention.

After the data from the medical claims and the pharmacy claims has been cleaned, as set forth above, the useful information is extracted from the claims and placed into a format convenient for computing the utilization score according to the healthcare resources modeling method 10 of the present invention (represented by block 16 in FIG. 1). In one embodiment of the present invention, this is done by creating various data files for use with the model of the present invention. FIG. 2 is a block diagram showing the various files that are created from the claims data in this embodiment.

As shown in FIG. 2, the data available to the healthcare resources modeling method 10 includes a physician claims file 24, a hospital claims file 26, a pharmacy claims file 28, and a key-member file 30. As described above, the physician claims file 24, the hospital claims file 26, and the pharmacy claims file 28 each contain information relating to healthcare provided by physicians, hospitals, and pharmacies, respectively, to a plan member. The key-member file 30 provides a unique identifier for each plan member and links that identifier to member numbers. In other words, a particular person may have been a plan member through different groups or under different plan options. The key-member file 30 is a data file that facilitates combining the claims submitted for that person under different groups or plan options. The key-member file 30 serves an important purpose of insuring that all available data is collected and used for modeling that person's healthcare utilization, in the healthcare resources modeling method 10. This use of a key-member file 30 insures that the maximum amount of data is available for use in the healthcare resources modeling method 10.

The physician claims file 24, the hospital claims file 26, and the pharmacy claims file 28, together with the key-member file 30, are used to create a number of other data files for use in the healthcare resources modeling method 10 of the present invention. As shown in FIG. 2, these other files include a medical data file 32, a pharmacy data file 34, a therapeutic pharmacy classification or GC3 data file 36, and miscellaneous data files 38. The medical data file 32, the pharmacy data file 34, the GC3 data file 36, and the miscellaneous data file 38 are created by extracting the data from the physician claims file 24, the hospital claims file 26, and the pharmacy claims file 28, and formatting them for convenient for use in the healthcare resources modeling method 10 of the present invention.

Figure 3:
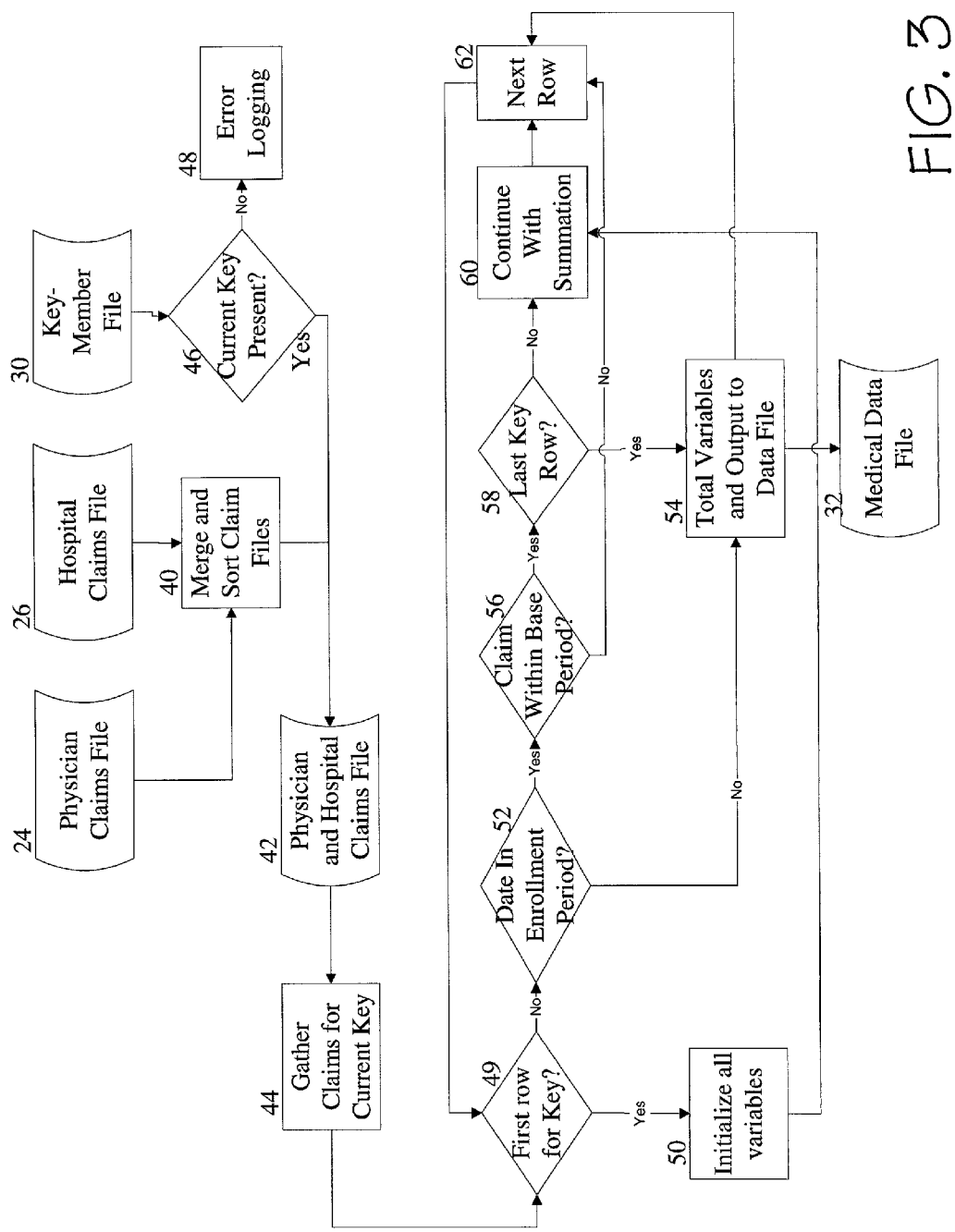
FIG. 3 is a flow chart illustrating the creation of the file containing the physician and hospital claims data.

FIG. 3 is a flowchart illustrating the process used to create the medical data file 32. As shown in FIG. 3, the data used in the creation of the medical data file 32 is drawn from the physician claims file 24, the hospital claims file 26, and the key-member file 30. In creating the medical data file 32, the physician claims file 24 and the hospital claims file 26 and to sort this merged file by key (the unique identifier for each person in the plan) and by the date on which service was provided by the physician or the hospital to the plan member (represented by block 40 in FIG. 3). This merged and sorted file is referred to as the merged physician and hospital claims file 42. Next, in creating the medical data file 32, the key-member file 30 is reviewed and claims are gathered for the current key (represented by block 44 in FIG. 3).

Initially, the process for gathering claims for the current key includes verifying the presence of the key in the key-member file 30 (represented by block 46 in FIG. 3). If the key is not present in the key-member file 30, that information is recorded in an error log (represented by block 48 in FIG. 3). After verifying that the current key is present in the key-member file 30, the data for the current claim is used in the creation of the medical data file 32.

If the current claim in the merged physician and hospital claims file 42 is the first claims for that particular key, all variables are initialized for that key (represented by block 50 in FIG. 3). In other words, one row is created in the medical data file 32 for that particular key. The variables that are extracted from the physician claims 26 and the hospital claims 28 and used in the creation of the medical data file 32 include some combination of those variables described above with respect to the physician claims file 24 and the hospital claims file 26.

After the relevant variables for the particular key are initiated, the data for the current claim is added to the appropriate variables (represented by block 60 in FIG. 3) and the process continues to the next row (represented by block 62 in FIG. 3) in the merged physician and hospital claims file 42. If the current claim is not the first row for the current key, the process asks whether the service date is within the enrollment period (represented by block 52 in FIG. 3). If not, the process assumes that it has reached the last claims for that key. It then totals up all variables (represented by block 54 in FIG. 3) and outputs the data to the medical data file 32, before continuing on to the next row (represented by block 62 in FIG. 3).

If the service date is within the enrollment period, the process asks whether the date of service of the current claim is within the base period (represented by block 56 in FIG. 3). If not, that claim is skipped and the process proceeds to the next claim. If so, the process asks whether the current claim is the last claims for the current key (represented by block 58 in FIG. 3). If it is the last claim for the current key, then the variables for that key are summed (block 54 in FIG. 3) and the results are output to the medical data file 32. If it is not the last claim for the current key, then the variables for the current claim are added to the totals for that particular key (block 60 in FIG. 3). Then, the process proceeds to the next row in the merged physician and hospital claims file 42 (represented by block 62 in FIG. 3).

This process continues until the end of the physician and hospital claims file 42 is reached. At this time, all relevant data has been extracted from the physician and hospital claims file 42 and has been placed in variables in the medical data file 32. The medical data file 32 includes one row for each key. The row includes totals for each relevant variable for that particular key.

Figure 4:
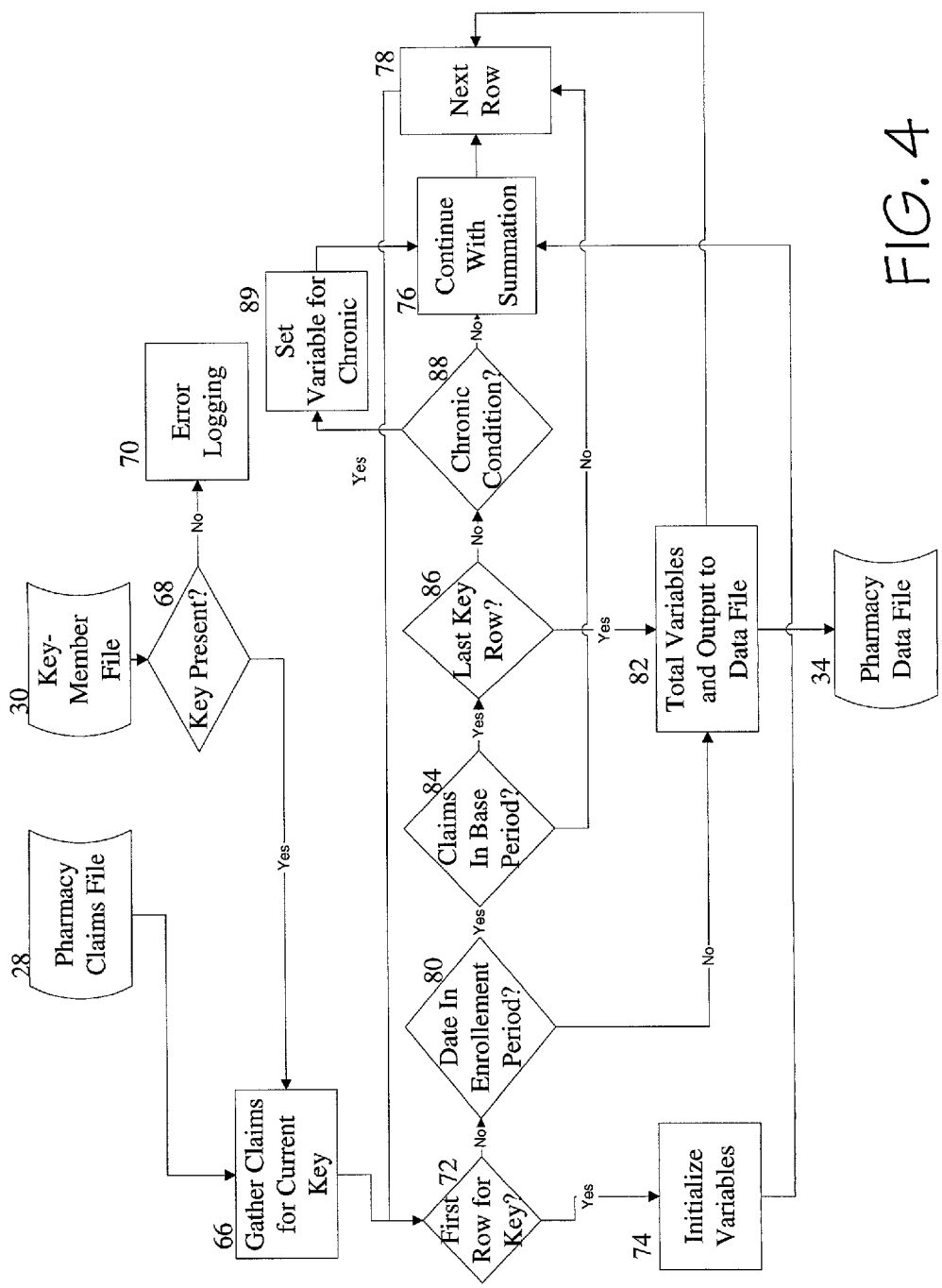
FIG. 4 is a flow chart showing the creation of a file containing the pharmacy claims data.

FIG. 4 is a flowchart illustrating the process used to create the pharmacy data file 34. As shown in FIG. 4, the data used in the creation of the pharmacy data file 34 is drawn from the pharmacy claims file 28 and the key-member file 30. Initially, in creating the pharmacy data file 34, the pharmacy claims file 28 is sorted by key and by date of service. Next, the pharmacy claims file 28 is reviewed by key to collect all claims for a particular key. Prior to performing this process, the presence of each key in the key-member file 30 is verified (represented by block 68 in FIG. 4). If a key is not present in the key-member file 30, that information is recorded in an error log (represented by block 70 in FIG. 3). After verifying that the current key is present in the key-member file 30, the data for the current claim is used in the creation of the pharmacy data file 34.

If the current claim in the pharmacy claims file 28 is the first claim for that particular key (see block 72 in FIG. 4), all variables are initialized for that key (represented by block 74 in FIG. 4). In other words, one row is created in the pharmacy data file 34 for that particular key. The variables in the pharmacy data file 34 include some subset of those described above, with reference to the pharmacy claims file 28. After the relevant variables for the particular key are initiated, the data for the current claim is added to the appropriate variables (represented by block 76 in FIG. 4) and the process continues to the next row (represented by block 78 in FIG. 4) in the pharmacy claims file 28.

If the current claim is not the first row for the current key, the process asks whether the service date is within the enrollment period (represented by block 80 in FIG. 4). If not, the process assumes that it has already processed the last claim for that key. It then skips the current claim and totals up all variables (represented by block 82 in FIG. 4) and outputs the data to the pharmacy data file 34, before continuing on to the next row (represented by block 78 in FIG. 4). If the service date is within the enrollment period, the process asks whether the date of service of the current claim is within the base period (represented by block 84 in FIG. 4). If not, that claim is skipped and the process proceeds to the next claim.

If the date of service is within the base period, the process asks whether the current claim is the last claim for the current key (represented by block 86 in FIG. 4). If it is the last claim for the current key, then the variables for that key are summed (block 82 in FIG. 4) and the results are output to the pharmacy data file 34. If the current claim is not the last claim for the current key, the process analyzes whether the current claim is for treatment of a chronic condition (represented by block 88 in FIG. 4). If so, a variable is set with a value indicating the presence of a chronic condition (represented by block 89 in FIG. 4). Chronic medical conditions, as opposed to acute medical conditions, are those that tend to be long lasting or ongoing. Next, the data for the current claim is added to the summation (block 76 in FIG. 4), and the process proceeds to the next row in the merged pharmacy claims file 28 (represented by block 78 in FIG. 4).

This process continues until the end of the pharmacy claims file 28 is reached. At this time, all relevant data has been extracted from the pharmacy claims file 28 and been placed in variables in the pharmacy data file 34. The pharmacy data file 34 includes one row for each key. The row includes totals for each relevant variable for that particular key.

Figure 5:
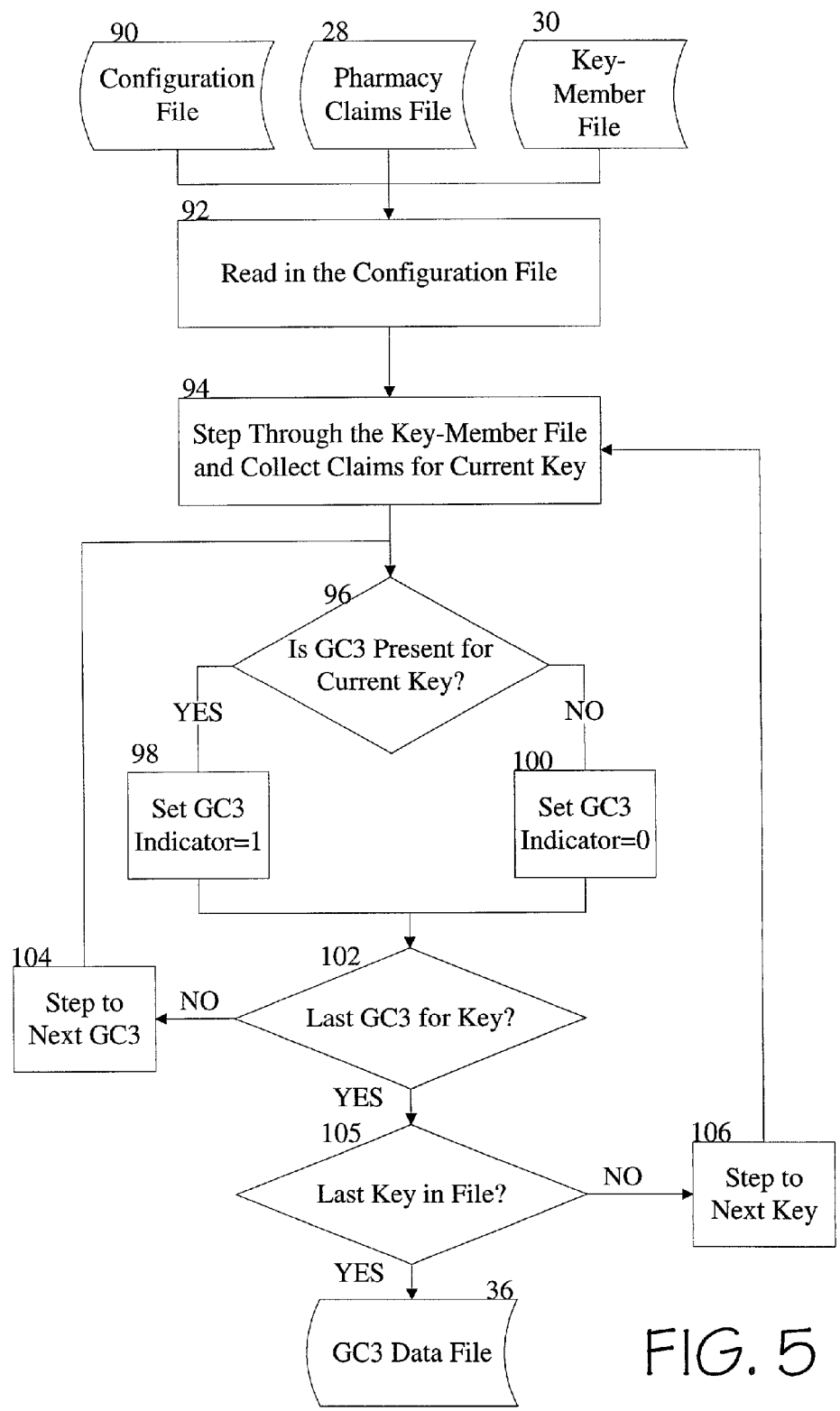
FIG. 5 is a flow chart illustrating the creation of a file containing GC3 data.

FIG. 5 is a flowchart illustrating the process used to create the therapeutic pharmacy classification or GC3 data file 36. The GC3 data file 36 contains categorical information on the pharmacy claims submitted for each member. The GC3 process is a process known in the art for mapping the approximately 150,000 NDC codes for prescribed medications into related therapeutic categories. Any other method known in the art for mapping drug codes into therapeutic pharmacy classes could also be used with the present invention. For purposes of convenience, the term "GC3" is used throughout the remainder of this specification, even though other systems could be used equally as well.

As shown in FIG. 5, the pharmacy claims file 28, the key-member file 30, and a configuration file 90 are used during the creation of the GC3 data file 36. The structure and the data content of the GC3 data file 36 are determined by the configuration file 90. The configuration file 90 contains the GC3 codes and the keys that are of interest for performing the healthcare resources modeling method 10 of the present invention. The use of the configuration file 90 allows the data collected in the GC3 data file 36 to be changed depending on the codes of interest for a particular application. After creation is complete, the GC3 data file 36 includes one row for each key and one column for each GC3 code of interest, as specified by the configuration file 90.

As shown in FIG. 5, in creating the GC3 data file 36, the configuration file 90 is read (represented by block 92 in FIG. 5). The configuration file 90 determines the ultimate structure of the GC3 data file 36 by specifying which GC3 codes are to be included in the file. Next, as specified in block 94 in FIG. 5, all claims in the pharmacy claims file 28 for the first key in the key-member file 30 are collected, and the NDC codes specified in those claims are converted into the corresponding GC3 code, using the GC3 coding process described above and as generally known in the art.

The collected GC3 codes for the first key are then examined to determine if the first GC3 code specified by the configuration file 90 is present (represented by block 96 in FIG. 5). If the first GC3 code is present, an indicator for that GC3 code is set equal to one in the GC3 data file 36 (as shown in block 98 in FIG. 5). If the GC3 code is not present, the indicator for that GC3 code is set equal to zero in the GC3 data file 36 (as shown in block 100 in FIG. 5). Next, the process asks whether the current GC3 code is the last code of interest for the current key (represented by block 102 in FIG. 5). If the current GC3 code is not the last code of interest for the current key, the process moves to the next GC3 code of interest and returns to analyze whether that GC3 is present (block 96). This process continues until the last GC3 code of interest for the current key is reached.

When the last GC3 code of interest for the current key is reached, the process asks whether the last key in the key-member file 30 has been reached (represented by block 105 in FIG. 5). If the last key has not been reached, the process moves to the next key in the key-member file 30 (shown in block 106 in FIG. 5) and returns to block 94 in the flowchart shown in FIG. 5. Here the pharmacy claims are collected from the pharmacy claims file 28 for the new current key and converted to appropriate GC3 codes, and the analysis proceeds for the current key, as explained above. When the last key in the key-member file 30 is reached, the process shown in FIG. 5 terminates, and the GC3 data file 36 is complete.

Figure 6:
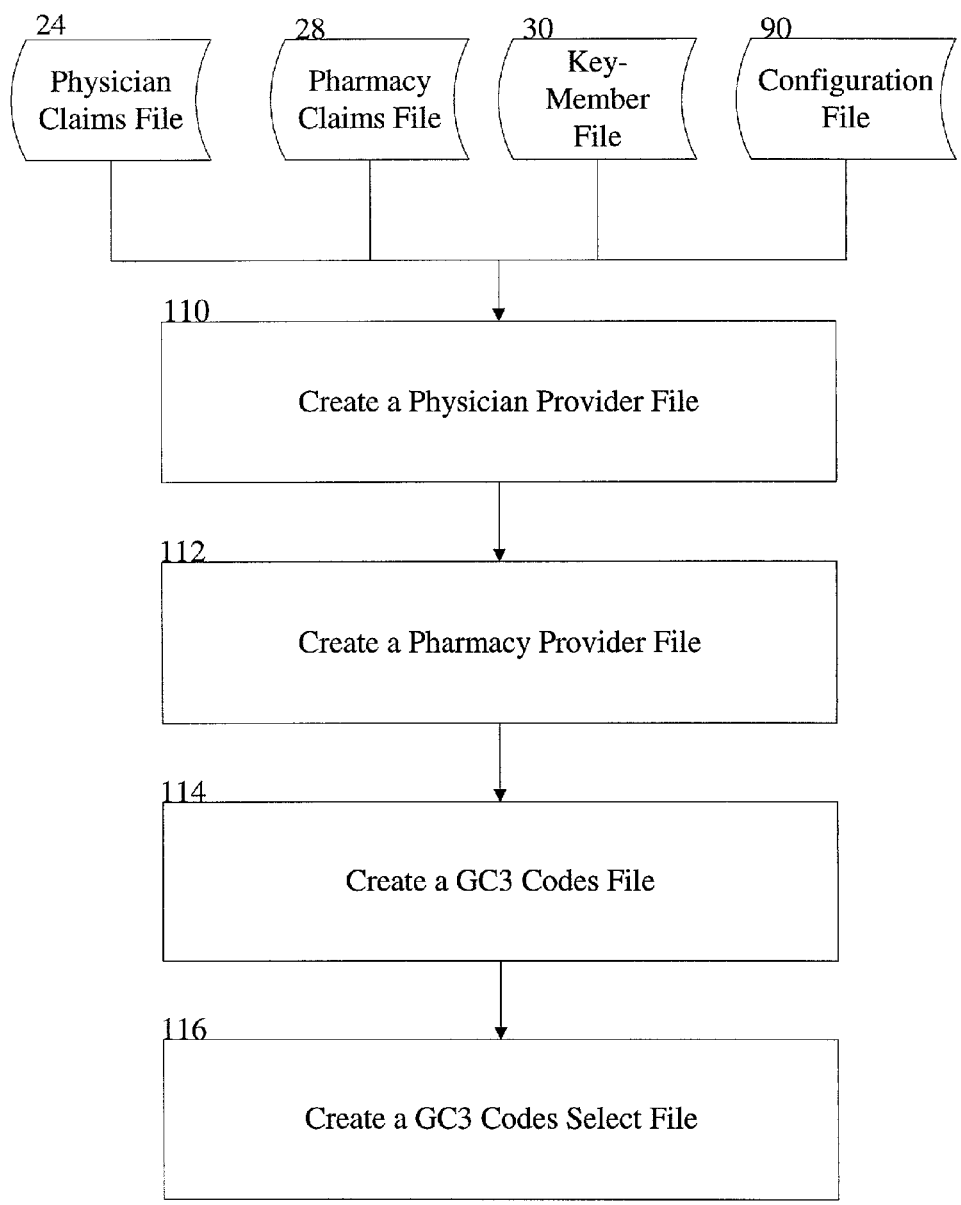
FIG. 6 is a block diagram showing a creation of miscellaneous data files according to the present invention.

As shown in FIG. 2, the final aspect of the creation of data files for use in the healthcare resources modeling method 10 of the present invention is to create various other data file (block 38 in FIG. 2). FIG. 6 is a block diagram showing the other data files created. As shown in FIG. 6, the other data files are created from data drawn from the physician claim file 24, the pharmacy claim file 28, the key-member file 30, and the configuration file 90. Once again, the configuration file 90 contains information on the format and content of the various other files created. The other files created will vary depending upon the particular desired results and the application for those results. In one embodiment, as shown in FIG. 6, the creation of other data files includes creating a physician provider file (block 110 in FIG. 6), creating a pharmacy provider file (block 112 in FIG. 6), creating a GC3 codes file (block 114 in FIG. 6), and creates a selected GC3 codes file (block 116 in FIG. 6).

As shown in FIG. 6, one of the miscellaneous data files created is the physician provider file 110. In one embodiment, the physician provider file 110 contains a row for each key from the key-member file 30 of interest, as specified by the configuration file 90. In this file, each key is assigned a number corresponding to the number of unique physician providers submitting claims (as contained in the physician claims file 24) for the plan number corresponding to that key. The physician provider file is created by stepping through the key-member file 30, gathering claims from the physician claims file 24 for the current key, counting the number of unique physician providers for the current key, and recording the result in the physician provider file. In one embodiment, the pharmacy provider file 112 is created in basically the same manner, except the data is drawn from the pharmacy claims file 28. The pharmacy provider file 112 has the same format as the physician provider file 110, namely one row for each key in the key-member file 30 corresponding to the number of unique pharmacy providers. The physician provider file 110 and the pharmacy provider file 112 are useful in the healthcare resources modeling method 10 of the present invention because the number of unique providers used by a plan member is relevant to modeling healthcare utilization.

As also shown in FIG. 6, another of the miscellaneous files is the GC3 codes file 114. In one embodiment, the GC3 codes file 114 contains a row for each key from the key-member file 30 of interest, as specified by the configuration file 90. In this file, each key is assigned a number that corresponds to the number of distinct GC3 codes prescribed to the plan member. The GC3 codes file 114 is created by stepping through the key-member file 30, gathering claims from the pharmacy claims file 28 for the current key, converting the NDC codes in the pharmacy claims to GC3 codes, counting the number of GC3 codes for the current key, and recording the result in the GC3 codes file 114. The GC3 codes file 114 is useful in the healthcare resources modeling method 10 of the present invention, because the total number of GC3 code medications prescribed to a plan member is relevant to the number of healthcare problems and to healthcare resources utilization.

In one embodiment, the GC3 codes select file 116 is created in basically the same manner as the GC3 codes file 114. The GC3 codes select file 116 differs from the GC3 codes file 114 in that the select file 116 contains the total number of GC3 codes specified by the configuration file 90 for a given plan member. In other words, the configuration file 90 specifies which of the GC3 codes are of the most importance in modeling healthcare utilization, and the total number of these codes are placed in the GC3 codes select file 116. In one embodiment, the selected GC3 codes are those that relate to chronic or ongoing conditions (as opposed to acute conditions). Chronic conditions are better predictors of future healthcare utilization because treatment of these conditions tends to continue long term. The GC3 codes relating to medications prescribed for chronic conditions are therefore often the most useful in modeling healthcare utilization.

A member data file is also used in the modeling method of the present invention. The member data file includes basic information about a member including name, age, gender, and address. Typically, the member file includes a combination of the fields or variables shown in Table 2 below. In one embodiment of the present invention, the member file includes all of the fields shown in Table 2.

TABLE 2

Member Data File Variables

| Variable | Description |
| --- | --- |
| KEY | The member's unique identifier |
| MEMBER ID | The member's plan identifier |
| DATE OF BIRTH | The member's date of birth |
| GENDER | The member's gender |
| MEMBER EFF. DATE | The effective date of the member's coverage |
| MEMBER EXP. DATE | The expiration date of the member's coverage |
| ADDRESS | The member's address |
| HOME PHONE | The member's home |
| FIRST NAME | The member's first name |
| LAST NAME | The member's last name |
| AGE | The member's age |

At this point, the conversion process of the healthcare resources modeling method 10 of the present invention, as represented by block 16 of FIG. 1, is complete. Next, as illustrated by block 18 in FIG. 1, a utilization score is computed for each member, using the data files that have been created.

The data files, available at this point in the process, are now used to compute a utilization score. The scoring technique of the present invention is generally based on the following formula:

$$\text{Score} = f(BOI, EV)$$

where score is the utilization score, BOI is the burden of illness, and EV represents measures of one or more explanatory variables. In one embodiment, the scoring technique of the present invention is based on a multiple linear regression equation as shown below:

$$\text{Score} = b_0 + \left( \sum_{i=1}^{n} b_i \cdot EV_i \right) + b_{n+1} \cdot BOI$$

where b are linear regression coefficients, i is the current explanatory variable, and n is the number of explanatory variables present in a given utilization model. The explanatory variables typically include those relating to age, gender, trending factors, variables measuring patterns in resource utilization, and variables that measure the interaction between other available variables. An advantage of the scoring technique of the present invention lies in its modularity, which gives it the flexibility to be readily modified for different applications. In the method of the present invention, the various components of the scoring model are assigned coefficients depending upon their overall importance to the score.

Figure 7:
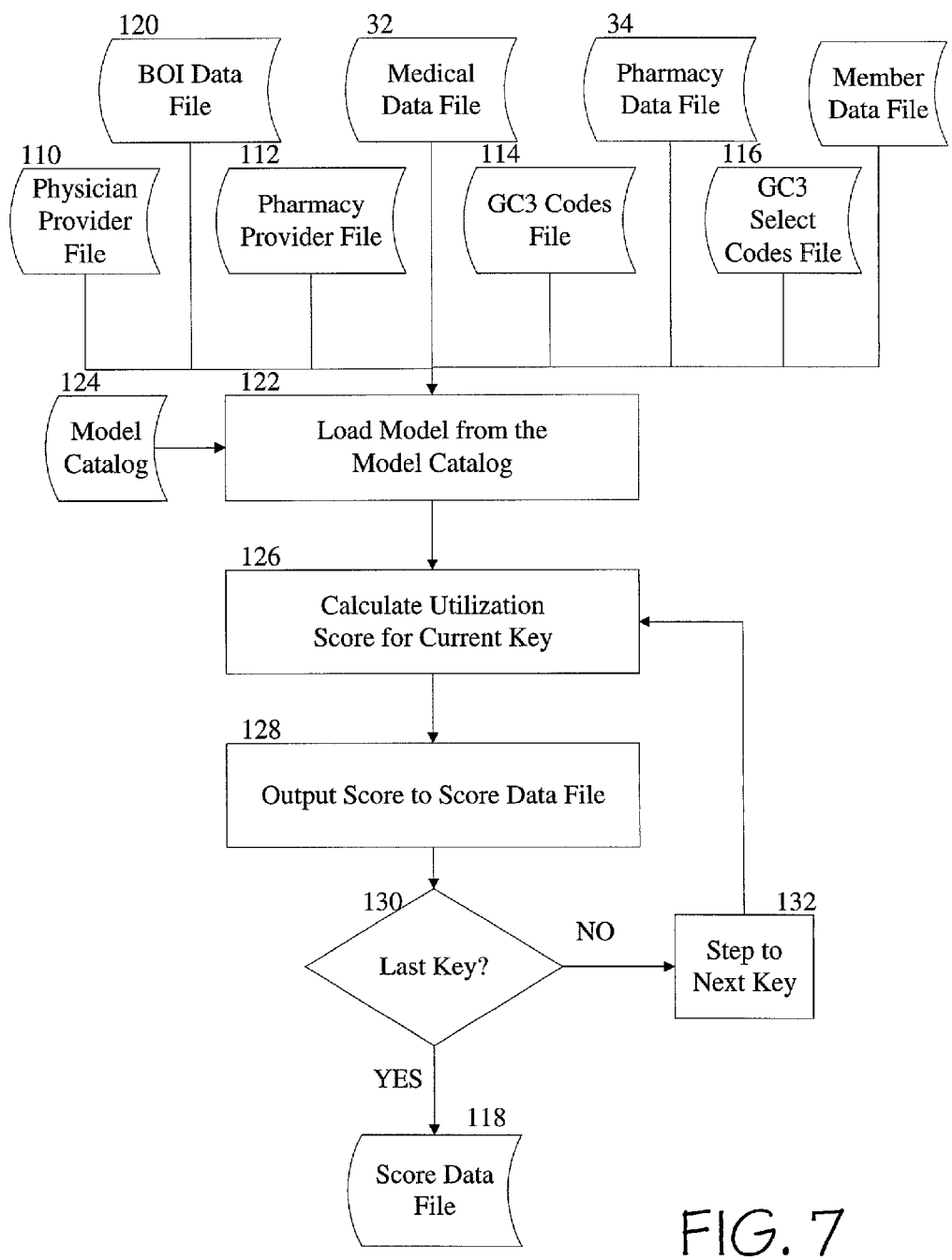
FIG. 7 is a flow chart showing the scoring calculation according to the present invention.

FIG. 7 is a flowchart illustrating the calculation of a utilization score according to the healthcare resources modeling method 10 of the present invention. As shown in FIG. 7, the various data files that are available for use in calculating a score for each member and creating a score data file 118 include a BOI data file 120, the medical data file 32, the pharmacy data file 34, the physician provider file 110, the pharmacy provider file 112, the GC3 codes file 114, the GC3 select codes file 116, and the member data file.

Initially, in calculating the utilization scores, the scoring model is loaded from a model catalog 124 (represented by block 122 in FIG. 7). The model catalog 124 specifies which of the available data files, and which particular aspects of those file, are used in calculating the utilization score. In other words, it specifies which components of the above scoring equation are used in generating the utilization score. The model catalog 124 also specifies the weight (represented by the coefficients "b" in the above equation) to be attributed to each piece of information in the overall calculation. Next, in the creation of the score data file 118, the utilization score is calculated for the current key (represented by block 126 in FIG. 7). This calculation is described in greater detail below. Next, the score for the current key is read into the score data file 118. This process continues until a score has been calculated and read into the score data file 118 for every key.

If required by the current scoring model, the age and gender of the current member are extracted from the member data file (shown in Table 2 above) for use in performing the scoring calculation. The burden of illness portion and the explanatory variables portion of the equation are derived as explained below.

The burden of illness portion of the scoring calculation is represented by the BOI data file 120. The BOI data file 120 contains a number for each plan member that measures the quantity of disease operative in the member as derived from claims data (some combination of medical claims and pharmacy claims) submitted for the plan member during the base period.

Next, the calculation of the burden of illness will be discussed. There are several methods of calculating the burden of illness consistent with the teachings of the present invention, including using pharmacy data only, using medical data only, and using a combination of all claims data available. At least one embodiment of each of these methods are discussed in greater detail below.

Figure 8:
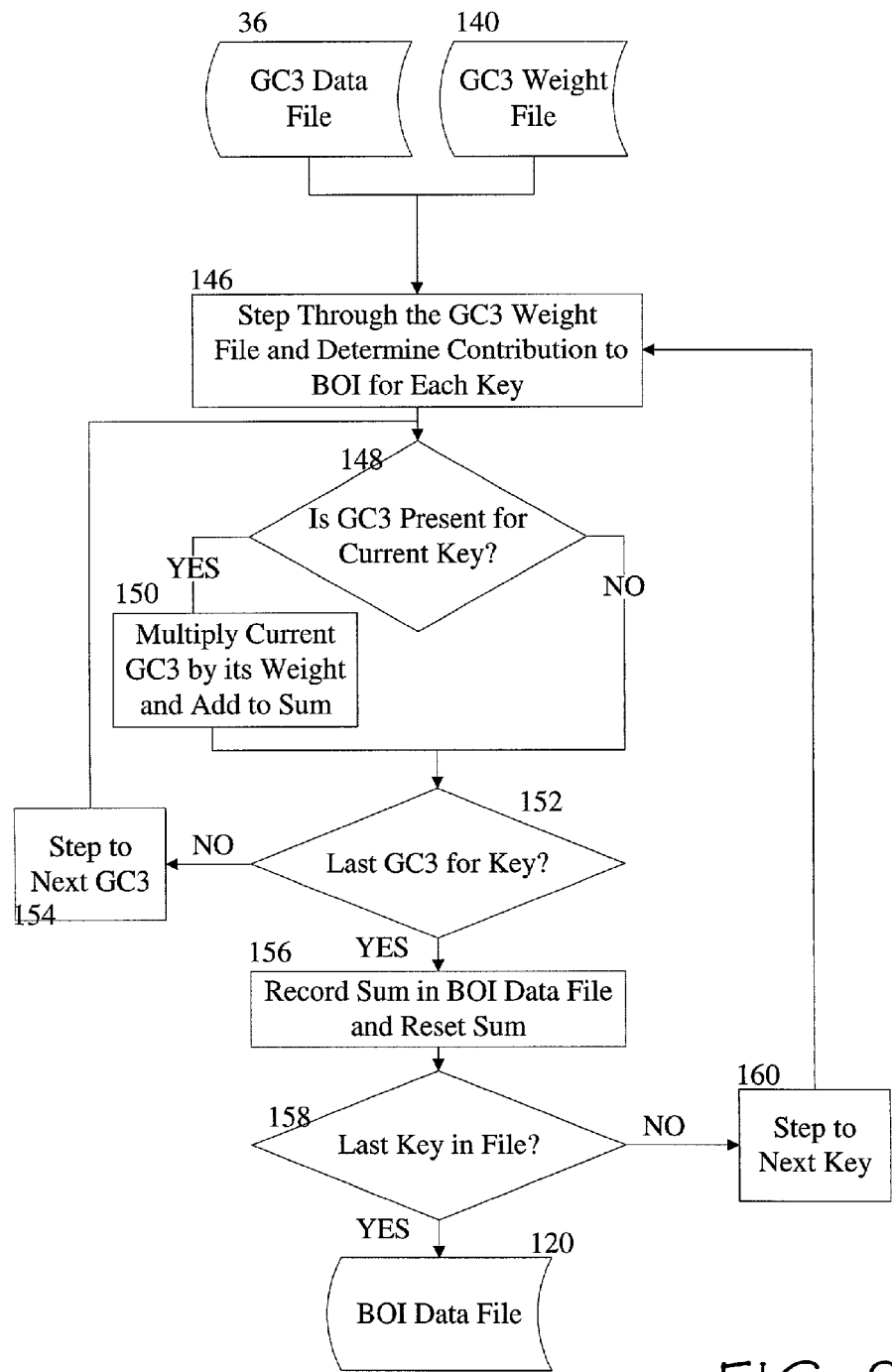
FIG. 8 is a flow chart showing the creation of a BOI data file according to the present invention.

FIG. 8 is a flowchart illustrating the creation of the BOI data file 120, according to a first embodiment of the present invention. In this embodiment, only data from the pharmacy claims file 28 is used. As shown in FIG. 8, the BOI data file 120 is calculated using data drawn from the GC3 data file 36 and a GC3 weight file 140. The GC3 data file 36 was described above, with reference to FIG. 5. This file indicates, for each plan member, whether a medication falling into each GC3 category was provided during the relevant time period. The GC3 weight file 140 is introduced here for the first time.

In one embodiment, the GC3 weight file 140 is generated by estimating the contribution weight associated with the presence of each GC3 category in a member's claims. In one embodiment, the weights are derived using a multiple regression method, where generally the dependent variable is total costs from medical and pharmacy claims for a target period from a benchmark population and the independent variables are dummy variables (e.g., zero or one) indicating the presence or absence of the GC3 category for this member in a base period. The resulting b values from the regression are used as the GC3 weights. In a further embodiment of the present invention, the dependent variable is a subset of total costs representing only those costs resulting from chronic illness.

As shown in FIG. 8, initially, in creating the BOI data file 120, a GC3 weight lookup is performed (represented by block 146 in FIG. 8) for each GC3 category present for the current member. This lookup involves stepping through the GC3 data file 36 (which contains the GC3s present for each plan member key). For each GC3 code in the GC3 data file 36, the process asks whether the file indicates the code was present (represented by block 148 in FIG. 8). If so, the weight of the current GC3 is extracted from the GC3 weight file 140 and added to a variable indicating the burden of illness (represented by block 150 in FIG. 8). In another embodiment, this process is performed by multiplying the corresponding weight from the GC3 weight file 140 by the value present in the GC3 data file 36 (one if the GC3 category was present for the member, and zero if the GC3 category was not present in the member's pharmacy claims). This will result in a product of zero if the GC3 category was not present in the member's pharmacy claims.

This process continues until the last GC3 is reached for the current key (blocks 152 and 154 in FIG. 8). When the last GC3 for the current key is reached, the variable, which is a summation of weights for each GC3, is written into the BOI data file 120 and is reset (represented by block 156 in FIG. 8). Next, the process asks whether this is the last key in the GC3 data file 36 (represented by block 158 in FIG. 8). If the current key is not the last key, the process increments to the next key (block 160) and repeats the process for that key (block 146). When the last key is reached, the creation of the BOI data file 120 is complete. The complete BOI data file 120 includes a row for each key and a column providing the sum of the weights for each GC3 code present for that plan member key. The burden of illness for each plan member, as stored in the BOI data file 120, is then used, either alone or in conjunction with other explanatory variables, to calculate a utilization score, as explained in further detail below.

In another embodiment of the present invention, the process of calculating a burden of illness score only looks at those GC3 codes that are present in the GC3 select codes file 116, as discussed above with respect to FIG. 7. In other words, only those GC3 codes that configuration file 90 specifies are used. For example, in one embodiment, the GC3 codes specified in the GC3 select codes file 116 include those likely to correspond to chronic medical conditions, because those codes provide the best predictive estimate of future healthcare utilization.

A second embodiment of the healthcare resources modeling method 10 of the present invention relates to calculating a burden of illness based on data from only medical claims (i.e., data from the physician claims file 24 and the hospital claims file 26). In this second embodiment of the present invention, a CCG data file is created. The CCG data file includes a wide variety of fields including a field for each of several medical claim classifications of similar medical claims. The use of a medical claim classification scheme allows the over 14,000 International Classification of Diseases ("ICD-9") codes to be placed into a more manageable number of related groups. In one embodiment of the present invention, the medical claim classifications used are Clinical Care Groups. Those skilled in the art will recognize that alternative claim classification schemes can be used.

Clinical Care Groups ("CCGs") are an Ingenix innovation for classifying diagnosis codes in medical claims. The CCG system allows the over 14,000 ICD-9 codes to be placed into a more manageable number of CCG classes, namely about 450 related disease or diagnosis categories. These approximately 450 CCG classes can be further reduced into about 120 CCG categories. Finally, these approximately 120 CCG categories can be placed into about 20 CCG specialties. Each of these levels provides various advantages in analyzing the claims data.

The CCG data file is created in generally the same manner as the GC3 data file 36 (shown in FIG. 5). Basically, all claims for the current member are gathered from the physician claims file 24 and the hospital claims file 26. The ICD-9 codes in these claims for the current member are then placed into the appropriate CCG classes, according to the Ingenix CCG claim classification scheme. When used as a classification scheme, CCGs only classify claims that result from a fact-to-face encounter between a provider and a member (e.g., an office visit). Next, each CCG class is analyzed for the presence of a claim to that CCG class for the present member. If a claim is present, a one is placed in the corresponding column of the CCG data file. If no claim is present for a given CCG class, a zero is placed in the corresponding column. This process repeats for all 450 CCG classes and for every plan member key present.

After the CCG data file is created, a medical BOI data file, based on the medical claims data, is calculated for each plan member, using generally the same technique as described with respect to FIG. 8. Instead of using the GC3 weight file 140, however, a CCG weight table is used. The CCG weight table is created by analyzing a set of plan member claims for a benchmark target period (or for a benchmark base period, when the target period is unknown), or for some other benchmark period, and calculating the average incremental cost in the benchmark period associated with the presence of a particular CCG for a plan member. Initially, in creating the medical BOI data file, a CCG weight lookup is performed for each CCG class present for the current member. This lookup involves stepping through the CCG data file (which contains the CCGs present for each plan member key). For each CCG code in the CCG data file, the process asks whether the file indicates the code was present. If so, the weight of the current CCG is extracted from the CCG weight table and added to a variable indicating the burden of illness value. In another embodiment, this process is performed by multiplying the corresponding weight from the CCG weight table by the value present in the CCG data file (one if the CCG class was present for the member, and zero if the CCG category was not present in the member's pharmacy claims). This will result in a product of zero if the CCG category was not present in the member's pharmacy claims. In another embodiment, the above process is performed at the CCG category level.

This process continues until the last CCG is reached for the current key. When the last CCG for the current key is reached, the variable, which is a summation of weights for each CCG, is written into the medical BOI data file and is reset. Next, the process asks whether this is the last key in the CCG data file. If the current key is not the last key, the process increments to the next key and repeats the process for that key. When the last key in the CCG data file is reached, the creation of the medical BOI data file is complete. The complete medical BOI data file includes a row for each key and a column providing the sum of the weights for each CCG code present for that plan member key. The burden of illness for each plan member, as stored in the medical BOI data file, is then used, either alone or in conjunction with other explanatory variables, to calculate a utilization score, as explained in further detail below.

In a third embodiment of the present invention, a burden of illness is calculated for each plan member, by using data from both pharmacy claims and medical claims, in the manner set forth above, and then combining the results (by summation, multiplication, or some other convenient form of combination) to obtain a combined burden of illness. This combined burden of illness is then used as the burden of illness component of the overall utilization score.

In a fourth embodiment of the present invention, data from both pharmacy claims and medical claims is again used. In this embodiment, however, as compared to the third embodiment, the data from both pharmacy claims and medical claims is used in a simultaneous manner to achieve a more sophisticated analysis, and thus a more accurate burden of illness for each plan member. In this embodiment the medical data file 32 and the pharmacy data file 34 are processed together through a CCG grouper and through a drug-disease matching ("DDM") application to associate all healthcare events (including drugs) embodied in the claims to a medical episode class (e.g., a CCG class).

In the second and third embodiments of the present invention, the CCG grouper was simply used as a claim classification scheme. In this fourth embodiment, on the other hand, the full medical episode capabilities of the Ingenix CCG grouper are used. Medical episode groupers take disease coded claims and place them into predetermined categories to facilitate analysis of the data. Basically, all claims that relate to the same general medical episode are placed in the same category. A medical episode grouper provides a more complete organization of medical events because it makes use of all available claims data while detecting important relationships between these claims. In one embodiment of the present invention, the medical episode grouper used is that described in greater detail in copending U.S. patent application Ser. No. 09/437,567, entitled "Method and System for Generating Statistically-Based Medical Provider Utilization Profiles," assigned to Ingenix, the assignee of the present application, and is hereby incorporated by reference in its entirety. Those skilled in the art will recognize that alternative groupers could be used that would preserve many aspects of the current invention.

The process of attaching CCGs (medical episode categories) to each of the pharmacy claims, requires that the medical and pharmacy data are first processed to attach a medical episode to each pharmacy claim. Typically, the medical and pharmacy claims W are processed through the Ingenix Drug-Disease Matcher ("DDM") application. This tool is described in greater detail in U.S. patent application Ser. No. 09/571,648, filed on May 15, 2000, entitled "System and Method of Drug Disease Matching," by Gerald Lutgen et al., assigned to Ingenix, the assignee of the present application, and is hereby incorporated by reference in its entirety. The DDM application operates to associate each pharmacy claim to the most probable ICD-9 code or codes found somewhere else in the members medical claims and then places these ICD-9 codes on the pharmacy claims. DDM associates ICD-9 codes to pharmacy claims by using "context sensitive" matching rules involving properties such as the time proximity of the pharmacy claim to certain medical claims, and documented indications for therapeutic pharmacy categories and specific diseases. Once the medical and pharmacy data has been processed by DDM, it can then be sent on to the medical episode grouper where both medical and pharmacy claims can now be grouped into medical episodes (e.g., CCG classes).

In this embodiment, the burden of illness is calculated in the same basic method described above with respect to the second embodiment. Once each of the pharmacy claims and medical claims has been associated with a CCG class, a CCG summary file is created for each plan member by inserting a zero in the file if the medical episode is not present for the member and inserting a one in the file if the medical episode is present for the member. Next, a burden of illness score is calculated by multiplying each CCG class in the CCG summary file by a weighting factor (e.g., the incremental cost associated with the presence of the particular CCG class). This episode-based burden of illness is then used in the calculation of the utilization score, as further explained below.

In a fifth embodiment of the present invention, the medical grouper process is applied to medical claims. Pharmacy claims are not present, so the DDM application is not performed. The burden of illness for each plan member is then calculated based on the medical claims data only.

Figure 9:
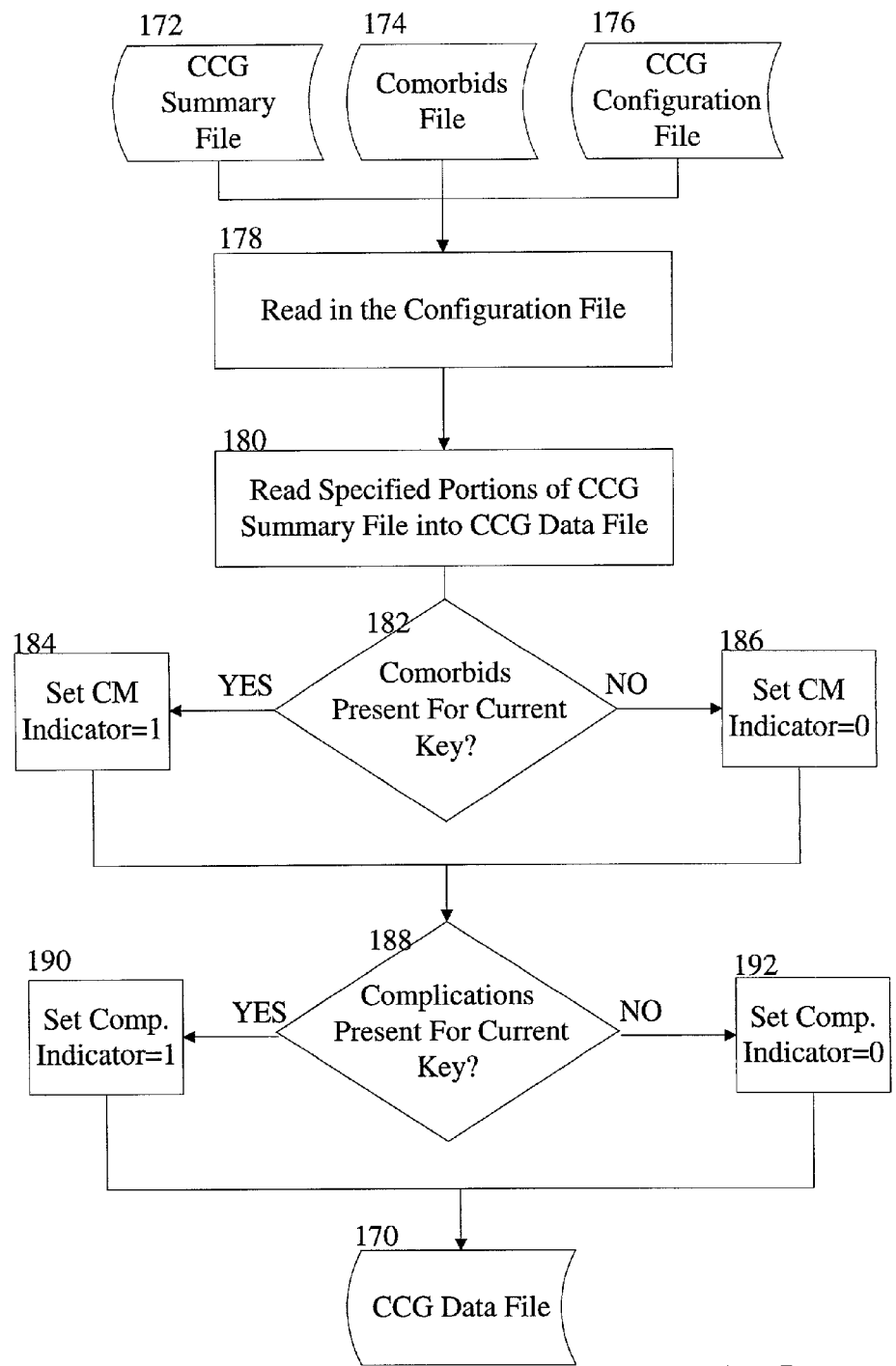
FIG. 9 is a block diagram showing the creation of a CCG file according to the present invention

An additional feature of the present invention, intended for use with the fourth or fifth embodiments, is illustrated in FIG. 9, which shows the creation of a CCG data file 170. The CCG data file 170 is used to calculate a burden of illness that takes W comorbidities and medical complications into account. Comorbidities and complications are medical episode classes within the same plan member within the base period of claims analyzed. Comorbidities are important because they tend to indicate more serious medical problems, and thus are predictive of greater future healthcare utilization. Likewise, complications are indicative of more serious medical problems, and thus are predictive of greater future healthcare utilization.

As shown in FIG. 9, the CCG data file 170 is drawn from three data files, a CCG summary file 172, a comorbids file 174, and a CCG configuration file 176. The comorbids file 174 includes a table for each of the CCG classes that has corresponding morbidity CCG classes and an identification of which CCG classes are comorbidity classes for a particular CCG class. The comorbids file 174 is created from knowledge of those in the medical profession on this subject. The CCG configuration file 176 indicates which of the CCG classes the model is interested in for a given application. The CCG configuration file 176 is similar to the configuration file 90 and functions in a similar manner. For example, in one embodiment, all the CCG configuration file 176 contains all CCG classes, and, in another embodiment, it contains only those CCG classes that correspond to a chronic medical condition, because those classes that correspond to a chronic medical condition are more accurate predictors of future healthcare utilization.

Initially, in creating the CCG data file 170, as shown in FIG. 9, the CCG configuration file 176 is read. Next, the portions of the CCG summary file 172 identified by the CCG configuration file 176 are read into corresponding columns in the CCG data file 170 (represented by block 180 in FIG. 9). Next, the comorbids file 174 is examined to determine whether comorbids are present for a particular plan member key (represented by block 182 in FIG. 9). In other words, the process determines whether the current plan member has claims in any combination of CCG classes that represent comorbidity. If comorbids are present for the current plan member key, a comorbidity field in the CCG data file 170 is set equal to one (represented by block 184 in FIG. 9). If no comorbids are present for the current plan member key, the comorbidity field is set equal to zero (represented by block 186 in FIG. 9). The CCG configuration file 176 sets up the number of comorbidity fields in the CCG data file 170. In one embodiment of the present invention, the CCG data file 170 includes only one comorbidity field. In this embodiment, if any comorbid combination of CCG classes is present for the current member, this field is set equal to one. In another embodiment, the CCG data file 170 includes multiple comorbidity fields, each representing a particular comorbidity combination. These combinations are set by the CCG configuration file 176 according their relevance to future healthcare utilization and thus their usefulness in the healthcare resources modeling method 10.

Next, the CCG summary file 172 is examined to determine whether complications are present for the current plan member key (represented by block 188 in FIG. 9). If complications are present, a complications indicator field in the CCG data file 170 is set equal to one (represented by block 190 in FIG. 9). If no complications are present, the complications indicator field is set equal to zero (represented by block 192 in FIG. 9). The CCG configuration file 176 sets up the number of complications fields in the CCG data file 170. In one embodiment of the present invention, the CCG data file 170 includes only one complications field. In this embodiment, if any complication is present for the current member, this field is set equal to one. In another embodiment, the CCG data file 170 includes multiple complications fields, each representing a particular complication. These complications are set by the CCG configuration file 176 according their relevance to future healthcare utilization and thus their usefulness in the healthcare resources modeling method 10.

In this embodiment, after the presence of comorbidities and complications has been identified, this information is used in the burden of illness calculation for each member of the plan. This information is used in one of two ways. In one embodiment, the CCG benchmark cost table includes separate columns for CCG classes having comorbids and separate columns for CCG classes having complications. In another embodiment, the CCG benchmark table includes factors for adjusting the cost upward based on the presence of a comorbid or a complication.

In one embodiment, after the burden of illness has been calculated for each plan member, a utilization score is calculated based on the burden of illness and other explanatory variables. Returning to FIG. 7, in creating the score data file 118 (containing the utilization scores), the scoring model is first loaded (block 122) from the model catalog 124. As described above, the model catalog 124 specifies the particular variables to be considered and the weight to be allocated to each, in calculating a utilization score. The healthcare resources modeling method 10 can be used for a variety of applications, as described further below, and different scoring methods may be more effective for different applications. The use of a model catalog 124 provides an easy and efficient mechanism for changing the scoring model.

Next, a utilization score is calculated (block 126 in FIG. 7) for the current key, based on the scoring model provided by the model catalog 124. In one embodiment, the score is based on burden of illness only. In one embodiment of the present invention, the score is based on the age and gender of the plan member (taken from the member data file) and the burden of illness as calculated and stored in the BOI data file 120. In another embodiment, other explanatory variables are also part of the scoring calculation, including the number of unique providers from the physician provider file 110 and the pharmacy provider file 112 and the number of relevant specialists visited. In another embodiment of the present invention, the trend factors are part of the scoring calculation, including the number and recency of medical and pharmacy claims for a given member. The recency of provider claims is the number of months for the current member since the last claim, either pharmacy or medical. In another embodiment, the number of different GC3 codes (taken from the GC3 codes file 114) and the number of different selected GC3 codes, indicating chronic medical conditions, (taken from the GC3 select does file 116) is also taken into account. In another embodiment, the total number of chronic medical episode classes acts as an explanatory variable. Persons of skill in the art will readily recognize that various other combinations of data may be used to perform the scoring calculations.

The utilization score is calculated by assigning a weight to each of the components of the equation. For example, a coefficient, or weight factor, is assigned to the burden of illness component and to each of the explanatory variable used in the model. The score is then obtained by summing, for each component of the model, the product of the weight for that component and the measurement for the component. In a first embodiment of the present invention, the coefficients are determined by experience and by empirical data.

In another embodiment of the healthcare resource modeling method 10 of the present invention, a calibration step is performed to determine the coefficients for the scoring equation. Calibration of the model is performed to derive accurate weighting factors or coefficients for each component of the scoring model. To perform calibrations of a model, it is necessary to have a "calibration data set" of claims data from both a base period and a target period for a benchmark population (in other words, the target period is a known target period). Multiple calibration methods are known to those skilled in the art and include methods such as multiple regression and logistic regression. In one embodiment, the coefficients of the model are obtained using multiple regression. In this embodiment, the dependent variable is total medical cost derived from medical and pharmacy claims in the target period, and the independent variables are the burden of illness, and one or more explanatory variables, obtained from claims in the base period. Once the coefficients are determined, the model is then applied to the extracted base period data to obtain a utilization score.

As shown in FIG. 1, the healthcare resources modeling method 10 next provides the score calculations to an application. The healthcare utilization scores, embodied in the score data file 118, are useful for several purposes. In a first embodiment of the present invention, the utilization data is used to identify those plan members that consume the most resources and place them into a cost containment system. For example, in one embodiment of the present invention, the score data file 118 is ranked from highest score (representing the greatest utilization prediction) to lowest score (representing the least utilization prediction). In one embodiment, any plan members exceeding a predetermined threshold are placed into a cost management system.

In one embodiment, the top three to five percent are placed into the cost management system identified and described in co-pending U.S. Provisional Patent Application Ser. No. 60/197,742, entitled "Care Coordination Health Care System," by Archelle Georgiou, which is hereby incorporated by reference into the present application in its entirety. As described in the referenced provisional application, the claims of these high risk members are closely monitored and any gaps in care are identified. Various intervention strategies are then implemented to fill any previous gaps in the healthcare provided to these high risk members. In other embodiments, other cost management or intervention systems are employed to reduce the future utilization of the identified high risk members.

In a second embodiment of the present invention, the utilization data is used as a tool in the underwriting process. In determining the premium for a particular group, the utilization scores for the entire group are used. The group's utilization scores are then compared to some average score for a larger member population to determine the relative risk of the group.

In a third embodiment of the present invention, the utilization data is used as part of the program seeking accreditation by the National Council on Quality and Accreditation ("NCQA"). To receive NCQA accreditation, a healthcare plan must show that (1) it is employing systematic efforts to improve care quality, (2) it is directing its efforts at specific identified diseases or conditions, and (3) it has documented improvements in care quality due to the efforts employed. The utilization scores calculated for each member pursuant to the present invention is one part of a systematic effort to improve care quality as required for NCQA accreditation.

The utilization scores obtained by using a burden of illness score based on both medical and pharmacy claims, processed through the medical episode grouping process, tends to provide more accurate results (because more data is considered, in a more robust manner), but it does so at a higher cost. The utilization scores obtained based on both claim types are used for all of the applications discussed previously including, identifying high-risk members, assisting in the underwriting process, and achieving NCQA accreditation.

In one embodiment of the present invention, the score data file 118, containing the member-by-member predictions of healthcare utilization, is created initially using only the data in the GC3 data file 36, as described above. This first score data file 118 is then ranked from greatest to least. In this embodiment, the plan members exceeding a predetermined threshold are identified. For example, in one embodiment, the top ten percent are identified. The utilization score for each of these members is then recalculated using the episoded CCG data file 170, to obtain scores based on a greater breadth of prior usage data. A benefit of this embodiment is that members can be scored more quickly and less expensively by performing a first cut based on pharmacy data alone, because executing the CCG process is more computationally expensive.

Figure 10:
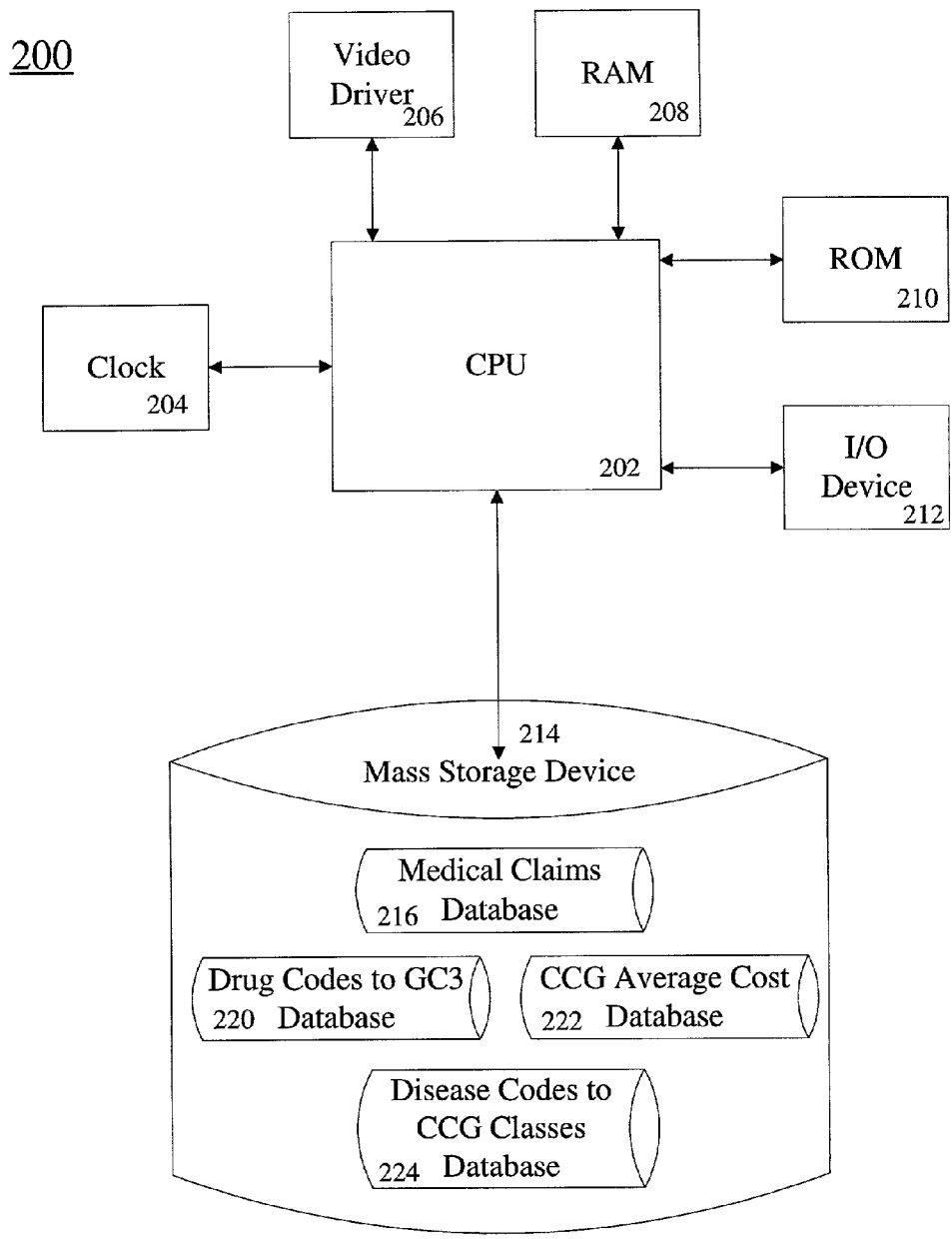
FIG. 10 is a block diagram showing a computerized system of the present invention.

FIG. 10 shows a block diagram of a predictive modeling system 200 according to the present invention. As shown in FIG. 10, the predictive modeling system 200 includes a central processing unit (CPU) 202, a clock 204, a video driver 206, a random-access memory (RAM) 208, a read-only memory (ROM) 210, an input/output (I/O) device 212, and a mass storage device 214. The clock 204, the video driver 206, the RAM 208, the ROM 210, the I/O device 212, and the mass storage device 214 are all in two-way communication with the CPU 202.

In one embodiment, the video driver 206 is coupled to a display device (not shown) for displaying the results generated by the predictive modeling system 200. In another embodiment of the present invention, no display device is included. The I/O device 212 allows the CPU 202 to exchange information with an external source (not shown). In one embodiment, the I/O device 212 is coupled to a keyboard, which allows an operator to initiate the system or modify certain parameters. In another embodiment, the I/O device 212 is connected to another computer system or to a network such as the Internet, which allows the CPU 202 to cause to results generated by the predictive modeling system 200 to be sent to another system for viewing or further processing.

The mass storage device 214 contains a medical claims database 216, a GC3 database 220, a CCG cost database 222, and a CCG classes database 224. These databases contain the information used by the predictive modeling system 200 to perform the healthcare resources modeling method 10, as described above.

During operation of the predictive modeling system 200, the CPU 202 executes code, located in the RAM 208 and the ROM 210, instructing the CPU 202 to carry out the methodology of the healthcare resources modeling method 10. The CPU 202 then executes the code, at a processing rate controlled by the clock 204. The CPU 202 draws the data necessary to perform the healthcare resources modeling method 10 either from files in the mass storage device 214 or by prompting the operator for input through the I/O device 212. Once the CPU 202 has all necessary information, it performs the calculations for burden of illness and utilization score, as discussed in detail above, and outputs the results. The results can either be sent through the video driver 206 to a display device, such as a video monitor or a printer, or sent out to another system through the I/O device 212.

While the preferred embodiment of the present invention has been described in detail, it should be apparent that many modifications and variations to it are possible, all of which fall within the true spirit and scope of the present invention. This application is intended to cover those variations. It is intended that this application be limited only by those limitations in the following claims.

We claim:

1. A method in a computer system for predicting a level of consumption of healthcare resources by modeling utilization of healthcare resources in a target period, the method comprising: a computer system performing the following:

compiling a plurality of provider claims for each of a plurality of members of a health plan, wherein the provider claims for the plurality of members occur within a base period and include a plurality of health conditions or diseases;

storing a plurality of disease categories representing a plurality of health conditions or diseases;

storing category weight data, wherein the category weight data comprises a weight value associated with each stored disease category, wherein each weight value associated with a stored disease category represents an average incremental cost for a plan member associated with the presence of the associated stored disease category during the base period;

for each of the plurality of health plan members, identifying each stored disease category present in the plurality of provider claims for the member;

calculating a burden of illness score for each member, wherein the burden of illness score is a number calculated by summing the stored weight values associated with each disease category identified in the member's provider claims;

storing at least one explanatory variable, wherein the explanatory variable is derived from demographic data or prior healthcare utilization data associated with the member;

computing a utilization score for each health plan member as a function of the burden of illness score and the at least one explanatory variable, wherein the utilization score is computed by assigning a weight factor to the burden of illness score and to the explanatory variable and summing (a) the product of the burden of illness score and its assigned weight factor and (b) the product of the explanatory variable and its assigned weight factor; and using the utilization score to predict healthcare resource consumption in the target period by at least one plan member.

2. The method of claim 1 wherein the disease categories are CCG categories.

3. The method of claim 1 further including the step of cleaning the provider claims to remove obviously erroneous information by comparing categories of the provider claims to acceptable values.

4. The method of claim 1 further including, prior to the calculating step, determining the presence of a plurality of medical episodes in the plurality of provider claims and grouping the plurality of provider claims into one or more groups based on a medical episode.

5. The method of claim 4 wherein the groups are Clinical Care Groups.

6. The method of claim 1 wherein the burden of illness score is adjusted to reflect the presence of a comorbidity in the member's plurality of provider claims.

7. The method of claim 1 wherein the burden of illness score is adjusted to reflect the presence of a complication in the member's plurality of provider claims.

8. The method of claim 1 wherein the burden of illness score is adjusted to reflect the age of the member.

9. The method of claim 1 wherein the burden of illness score is adjusted to reflect the gender of the member.

10. The method of claim 1 wherein the at least one explanatory variable is a number indicating in which of a plurality of age categories the member belongs.

11. The method of claim 1 wherein the at least one explanatory variable is a number indicating the gender of the member.

12. The method of claim 1, wherein the explanatory variable is a factor that indicates a number of claims representing a chronic disease for the member.

13. The method of claim 1 wherein the explanatory variable is a factor that indicates the recency of claims for the member.

14. The method of claim 1 wherein the explanatory variable is the sum of chronic medical costs from the medical claims.

15. The method of claim 1 further including calculating a relative risk for the member of a group by dividing the utilization score by an average utilization score for the group.

16. The method of claim 1 further including calculating a relative risk for the member of a group by dividing the utilization score by an average utilization score for a benchmark group.

17. The method of claim 1, further comprising the step of identifying a high risk set of members by selecting the members having utilization scores that exceed a predetermined level.

18. The method of claim 1, further comprising calibrating the model by comparing a computed utilization score against healthcare resource utilization for the target period.

19. The method of claim 1, further comprising, prior to the computing step, calibrating the model of a computed utilization score against healthcare resource utilization for a known target period, for only utilization due to chronic medical conditions.

20. A method in a computer system for determining consumption of healthcare resources by a plurality of plan members in a healthcare plan during a base time period, comprising: a computer system performing the following compiling pharmacy claims for each of a plurality members of a health plan, wherein the pharmacy claims for the plurality of members include a plurality of drug categories;

storing a plurality of drug categories;

storing category weight data, wherein the category weight data comprises a weight value associated with each stored drug category, wherein each weight value associated with a stored drug category represents an average incremental cost for a plan member associated with the presence of the associated stored drug category during the base period;

for each of the plurality of health plan members, identifying each stored drug category present in the plurality of pharmacy claims for the member;

calculating a burden of illness score for each member, wherein the burden of illness score is a number calculated by summing the stored weight values associated with each drug category identified in the member's pharmacy claims;

storing at least one explanatory variable, wherein the explanatory variable is derived from demographic data or prior healthcare utilization data associated with the member;

computing a utilization score for each health plan member as a function of the burden of illness score and the at least one explanatory variable, wherein the utilization score is computed by assigning a weight factor to the burden of illness score and to the explanatory variable and summing (a) the product of the burden of illness score and its assigned weight factor and (b) the product of the explanatory variable and its assigned weight factor; and using the utilization score to predict healthcare resource consumption by at least one plan member.

21. The method of claim 20, wherein the target period is later in time than the base period.

22. The method of claim 20, wherein the target period is the same time period as the base period.

23. The method of claim 20, further including the step of cleaning the claim data to remove obviously erroneous information by comparing categories of the data set to acceptable values.

24. The method of claim 20, wherein the drug categories correspond to GC3 pharmacy classes.

25. The method of claim 20, wherein pharmacy claims in the claim data are assigned to one of a plurality of groups based on a relationship to corresponding medical claims indicating the presence of the medical episode.

26. The method of claim 20, wherein the associated burden weight for at least one health condition is adjusted based on the age of each member.

27. The method of claim 20, wherein the associated burden weight for at least one health condition is adjusted based on the gender of the member.

28. The method of claim 20, wherein the associated burden weight for at least one health condition is adjusted based on an average incremental cost associated with a benchmark population.

* * * * *

UNITED STATES PATENT AND TRADEMARK OFFICE
CERTIFICATE OF CORRECTION

| | | |
|---|---|---|
| PATENT NO. | : 7,444,291 B1 | Page 1 of 1 |
| APPLICATION NO. | : 09/635911 | |
| DATED | : October 28, 2008 | |
| INVENTOR(S) | : Badri N. Prasad | |

It is certified that error appears in the above-identified patent and that said Letters Patent is hereby corrected as shown below:

| Column | Line | PTO | Should Read |
|---|---|---|---|
| 5 | 54 | "forgathering" | --for gathering-- |
| 13 | 65 | "claims w are" | --claims are-- |
| 14 | 40 | "w comorbidities" | --comorbidities-- |

Signed and Sealed this

Thirtieth Day of December, 2008

JON W. DUDAS
*Director of the United States Patent and Trademark Office*